United States Patent
Shetty

(10) Patent No.: US 11,364,274 B2
(45) Date of Patent: Jun. 21, 2022

(54) COMPOSITION FOR TREATMENT AND MANAGEMENT OF POLYCYSTIC OVARIAN SYNDROME AND METHOD OF PREPARATION THEREOF

(71) Applicant: Muniyal Ayurvedic Research Centre, Manipal (IN)

(72) Inventor: M Vijayabhanu Shetty, Karnataka (IN)

(73) Assignee: Muniyal Ayurvedic Research Centre, Manipal (IN)

(*) Notice: Subject to any disclaimer, the term of this patent is extended or adjusted under 35 U.S.C. 154(b) by 179 days.

(21) Appl. No.: 16/807,446

(22) Filed: Mar. 3, 2020

(65) Prior Publication Data

US 2020/0197477 A1    Jun. 25, 2020

Related U.S. Application Data

(60) Provisional application No. 62/814,047, filed on Mar. 5, 2019.

(51) Int. Cl.
| | | |
|---|---|---|
| *A61K 36/00* | (2006.01) | |
| *A61K 36/899* | (2006.01) | |
| *A61K 36/48* | (2006.01) | |
| *A61K 36/59* | (2006.01) | |
| *A61K 9/20* | (2006.01) | |
| *A61K 35/02* | (2015.01) | |
| *A61K 33/00* | (2006.01) | |
| *A61P 15/02* | (2006.01) | |
| *A61K 36/736* | (2006.01) | |

(52) U.S. Cl.
CPC ............ *A61K 36/899* (2013.01); *A61K 9/205* (2013.01); *A61K 33/00* (2013.01); *A61K 35/02* (2013.01); *A61K 36/48* (2013.01); *A61K 36/59* (2013.01); *A61K 36/736* (2013.01); *A61P 15/02* (2018.01)

(58) Field of Classification Search
CPC ................................ A61P 15/02; A61K 33/00
See application file for complete search history.

*Primary Examiner* — Qiuwen Mi

(74) *Attorney, Agent, or Firm* — Pilloff Passino & Cosenza LLP; Sean A. Passino; Rachel K. Pilloff

(57) ABSTRACT

Composition for the treatment and management of Polycystic ovarian syndrome and method of preparation thereof are disclosed herein. The disclosed Herbal composition includes herbs and minerals which facilitate in treating PCOS and PCOS associated symptoms. The composition comprises *Saraca indica, Symplocos racemosa, Boerhavia diffusa, Tinospora cordifolia, Terminalia arjuna, Saccharum officinarum* and *Commiphora mukul*, or extracts thereof; Shilajit; and bhasmas. The disclosed composition may also be instrumental in improving general reproductive health of an individual.

19 Claims, 4 Drawing Sheets

COMPOSITION FOR TREATMENT AND MANAGEMENT OF POLYCYSTIC OVARIAN SYNDROME AND METHOD OF PREPARATION THEREOF

CROSS REFERENCE TO RELATED APPLICATION

This application is based on and claims the benefit of U.S. Provisional Application 62/814,047 filed on 5 Mar. 2019, the contents of which are incorporated herein by reference in their entirety.

TECHNICAL FIELD

The embodiments disclosed in this specification relate to herbal compositions in the treatment and management of endocrine disorders, and more particularly in the treatment of polycystic ovarian syndrome and associated complications thereof. It also relates to the process of preparation of such composition.

BACKGROUND

Polycystic ovarian syndrome (PCOS) is a condition affecting many women at their reproductive age. PCOS incapacitates the uterine system thereby making it difficult for women to conceive. The condition may be characterized by enlarged ovaries caused due to the development of numerous fluid filled follicles around the eggs. Women having PCOS often exhibit menstrual irregularity and hyperandrogenism.

The excess androgen levels in women can cause adverse effects. Obesity, hypertension, amenorrhea, etc. are some of the undesirable effects. Hirsutism, alopecia and acne are the most prominent features of hyperandrogenism. Hirsutism is a condition where women as a result of elevated androgen levels develop hair on face, back and abdomen. Alopecia is another symptom wherein balding of head may occur. Facial acne is also a prominent and undesirable feature that may bother many women having PCOS.

Although, the causes of PCOS are not entirely clear, insulin resistance in some cases is considered to play a key role in the development of PCOS. Whatever the cause may be, PCOS ensued from the imbalance in levels of insulin and other hormones such as Luteinizing hormone, androgen, etc. can be a depressing and anxiety ridden situation.

Various allopathic treatments are known to overcome a few complications of PCOS. First line of treatment generally employed include medication such as Clomiphene, Metformin, Oral contraceptives, etc. These medications try to induce a state of normalcy by inducing ovulation, insulin sensitization, inhibiting hair growth, etc. However, these allopathic medications have been observed to cause hypersensitivity and other side effects and have not been observed to entirely treat all aspects associated with PCOS, thus creating a need for alternate therapy options that provide effective treatment without side effects.

Various ayurvedic treatment regimen involving methods such as Shodhana and Shamana have been instrumental in treating PCOS. The use of mushrooms, fenugreek, Panaxquinquefolius, Pfaffiapaniculada, etc in developing compositions to treat PCOS is also well-known. However, there exists a need for better methods to bring holistic healing and rejuvenation in PCOS patients.

Objects

The principal object of the embodiments disclosed herein is to provide a composition and method for the treatment of Polycystic ovarian syndrome (PCOS).

A second object of the embodiments disclosed herein is to provide a composition and method for the management of PCOS.

Another object of the embodiments disclosed herein is to provide a composition and method for the treatment of symptoms associated with PCOS.

A further object of the embodiments disclosed herein is to provide a composition and method for the treatment of gynecological disorders.

Yet another object of the embodiments disclosed herein is to provide a composition and method for improving reproductive health.

Furthermore, an object of the embodiments disclosed herein is to provide a herbal composition and a method for its preparation.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated in the accompanying drawings. The embodiments herein will be better understood from the following description with reference to the drawings, in which.

DETAILED DESCRIPTION

Figure 1:
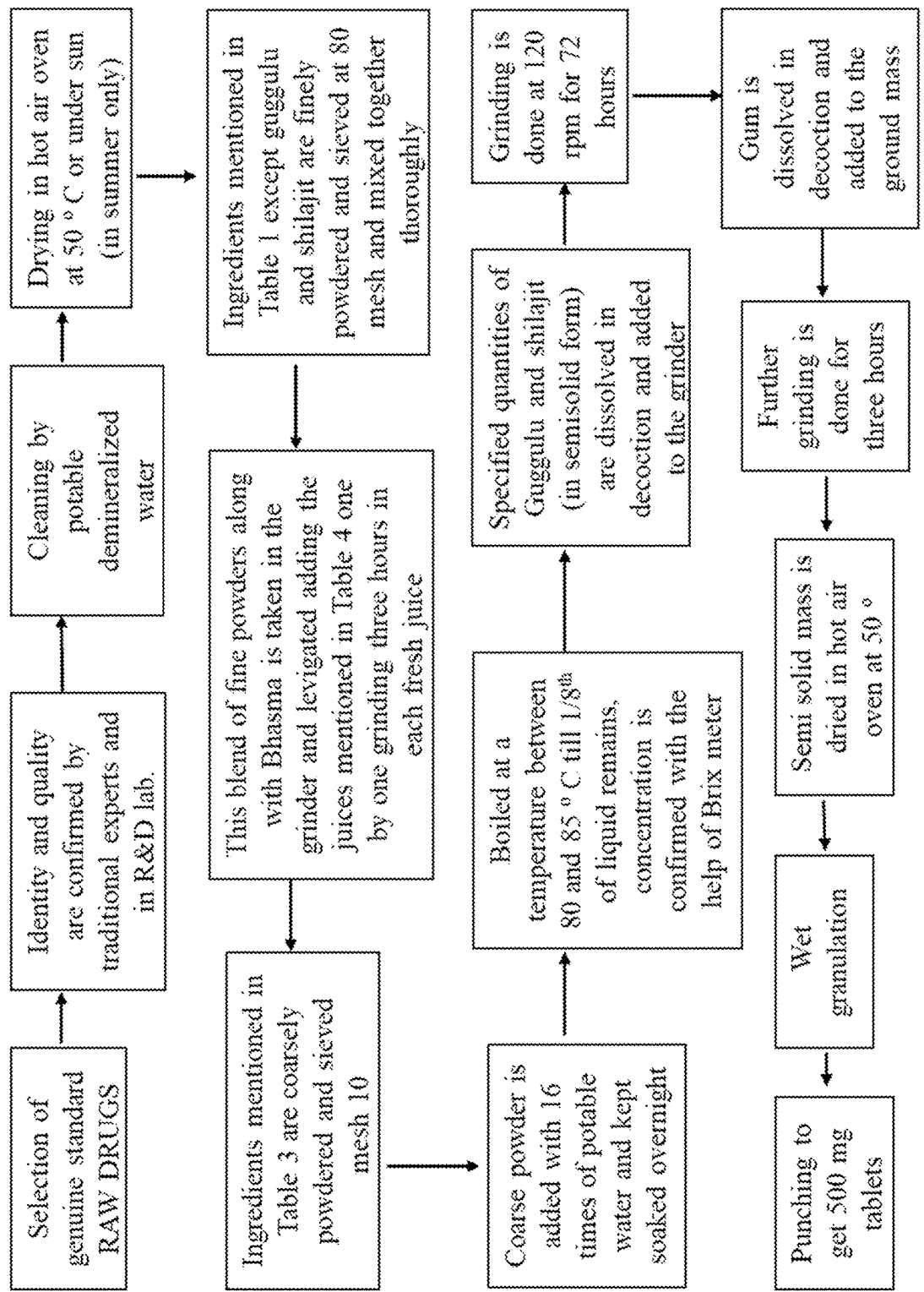
FIG. 1 depicts a flowchart for the preparation of fortified tablets, according to embodiments as disclosed herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve an herbal composition of therapeutic value, and a process for preparation of the composition. The herbal composition disclosed herein is useful in the treatment and management of Polycystic ovarian syndrome (PCOS). It has also been observed that the embodiments of the disclosed composition are effective in treatment and management of symptoms and complications associated with PCOS. Accordingly, embodiments of a method for treatment/management of such symptoms and complications associated with PCOS is also provided herein. The symptoms of PCOS include the generally known symptoms such as irregular menstrual cycle, hirsutism, alopecia, acne, obesity, hypertension, amenorrhea, etc. Further, the embodiments of the disclosed composition have also found to be effective in treatment of gynecological disorders such as female infertility, dysmenorrhoea, leucorrhoea, excess menstrual bleeding as seen in Dysfunctional Uterine Bleeding, etc. Furthermore, the embodiments disclosed herein also include a method for improving reproductive health of an individual.

Composition

The disclosed embodiments herein provide herbal composition having a combination of selected herbs and minerals. In an embodiment, the herbal composition includes herbs and minerals. In another embodiment, the herbal composition includes herbs, minerals and at least one alkali. In yet another embodiment, the herbal composition includes herbs, minerals, at least one alkali and at least one salt. In an embodiment, the herbal composition may further include one or more suitable excipient.

Herbs

In an embodiment, the composition comprises of *Saraca indica, Symplocos racemosa, Boerhavia diffusa, Tinospora cordifolia, Terminalia arjuna, Saccharum officinarum* and *Commiphora mukul*, or their extracts, or the active ingredients extracted from these herbs. In another embodiment, the composition further includes at least one herb selected from a group consisting of *Emblica officinalis, Terminalia chebula, Terminalia bellerica, Stereospermum suaveolens, Premna mucronata, Gmelina arborea, Aegle marmelos, Oroxylum indicum, Desmodium gangeticum, Uraria picta, Solanum indicum, Solanum xanthocarpum, Tribulus terrestris, Sida cordifolia, Nardostachys jatamansi, Acacia catechu, Rubia cordifolia, Hemidesmus indicus, Cedrus deodara, Withania somnifera, Pueraria tuberosa, Hydnocarpus laurifolia, Ficus glomerata, Dioscorea bulbifera, Cinnamomum camphora, Acorus calamus, Cyperus rotundus, Swertia chirata, Curcuma longa, Aconitum heterophyllum, Berberis aristata, Plumbago zeylanica, Coriandrum sativum, Piper longum, Embelia ribes, Piper chaba, Zingiber officinale, Piper nigrum, Operculina turpethum, Baliospermum montanum, Cinnamomum tamala, Cinnamomum zeylanicum* and *Bamboo manna*, or their extracts, or the active ingredients extracted from these herbs.

The composition may include a specific part of the herb (also referred as herb component) such as roots, flowers, fruits, stem, bark, resin, rhizome, whole plant, extract etc. In an embodiment, the composition may include heartwood of *Saraca indica*, stem bark of *Symplocos racemosa*, root of *Boerhavia diffusa*, stem of *Tinospora cordifolia*, stem bark of *Terminalia arjuna*, extract of *Saccharum officinarum*, oleo gum resin of *Commiphora mukul*, fruits of *Emblica officinalis*, fruits of *Terminalia chebula*, fruits of *Terminalia bellerica*, roots of *Stereospermum suaveolens*, roots of *Premna mucronata*, roots of *Gmelina arborea*, roots and fruit pulp of *Aegle marmelos*, roots of *Oroxylum indicum*, whole plant of *Desmodium gangeticum*, whole plant of *Uraria picta*, whole plant of *Solanum indicum*, whole plant of *Solanum xanthocarpum*, fruits of *Tribulus terrestris*, roots of *Sida cordifolia*, rhizome of *Nardostachys jatamansi*, heartwood of *Acacia catechu*, roots of *Rubia cordifolia*, roots of *Hemidesmus indicus*, heartwood of *Cedrus deodara*, roots of *Withania somnifera*, tuber of *Pueraria tuberosa*, seeds of *Hydnocarpus laurifolia*, stem bark of *Ficus glomerata*, tuber of *Dioscorea bulbifera*, sublimate crystals of *Cinnamomum camphora*, rhizome of *Acorus calamus*, roots of *Cyperus rotundus*, whole plant of *Swertia chirata*, rhizome of *Curcuma longa*, roots of *Aconitum heterophyllum*, roots of *Berberis aristata*, roots of *Plumbago zeylanica*, fruits of *Coriandrum sativum*, fruits and roots of *Piper longum*, roots and stem of *Piper chaba*, rhizome of *Zingiber officinale*, fruits of *Piper nigrum*, fruits of *Embelia ribes*, roots of *Operculina turpethum*, roots of *Baliospermum montanum*, leaves of *Cinnamomum tamala*, stem bark of *Cinnamomum zeylanicum* and secretion of *Bamboo manna*. However, it is also within the scope of the claims provided herein for the herbal composition to include other herb components such as leaf, flowers, etc. without otherwise deterring intended function of the herbal composition.

The herb component maybe included in the composition in any form that is generally known in the field. For example, the herb component may be dried, powdered, processed to form concentrates, extracts, sublimate etc. In an embodiment, the herb components are in the form of dry powder which is incorporated into the composition. In an embodiment, the herb components are in the form of a fine powder that is obtained by 80 mesh size sieves. Although, the composition disclosed in the various embodiments herein includes dried and powdered form of specific herb components as disclosed herein, minor modifications and variations to form and components used would be apparent to a person skilled in the art.

The herbs used in the disclosed composition may be included as powders form of whole herb components, as extracts of herbs, or as active ingredients extracted from herbs. The extracts of herbs may be prepared by techniques known in the field and may include aqueous extracts, alcoholic extracts (e.g.: ethanolic or methanolic extracts) or a combination of aqueous and alcoholic extracts. In an embodiment, the composition includes aqueous ethanolic extracts of the herbs disclosed herein.

In an embodiment, the composition includes *Saraca indica* in an amount ranging from 10 to 14 wt. %, *Symplocos racemosa* in an amount ranging from 8 to 12 wt. %, *Boerhavia diffusa* in an amount ranging from 8 to 12 wt. %, *Tinospora cordifolia* in an amount ranging from 2 to 5 wt. %, *Terminalia arjuna* in an amount ranging from 2 to 5 wt. %, *Saccharum officinarum* in an amount ranging from 2 to 5 wt. %, and *Commiphora mukul* in an amount ranging from 5 to 8 wt. %, of the total weight of the composition.

In another embodiment, the composition may further include at least one ingredient selected from a group consisting of *Emblica officinalis* in an amount of ≤2 wt. %, *Terminalia chebula* in an amount of ≤2 wt. %, *Terminalia bellerica* in an amount of ≤2 wt. %, *Stereospermum suaveolens* in an amount of ≤2 wt. %, *Premna mucronata* in an amount of ≤2 wt. %, *Gmelina arborea* in an amount of ≤2 wt. %, *Aegle marmelos* in an amount of ≤2 wt. %, *Oroxylum indicum* in an amount of ≤2 wt. %, *Desmodium gangeticum* in an amount of ≤2 wt. %, *Uraria picta* in an amount of ≤2 wt. %, *Solanum indicum* in an amount of ≤2 wt. %, *Solanum xanthocarpum* in an amount of ≤2 wt. %, *Tribulus terrestris* in an amount of ≤2 wt. %, *Sida cordifolia* in an amount of ≤2 wt. %, *Nardostachys jatamansi* in an amount of ≤3 wt. %, *Acacia catechu* in an amount of ≤3 wt. %, *Rubia cordifolia* in an amount of ≤3 wt. %, *Hemidesmus indicus* in an amount of ≤2 wt. %, *Cedrus deodara* in an amount of ≤3 wt. %, *Withania somnifera* in an amount of ≤2 wt. %, *Pueraria tuberosa* in an amount of ≤2 wt. %, *Hydnocarpus laurifolia* in an amount of ≤2 wt. %, *Ficus glomerata* in an amount of ≤2 wt. %, *Dioscorea bulbifera* in an amount of ≤2 wt. %, *Cinnamomum camphora* in an amount of ≤2 wt. %, *Acorus calamus* in an amount of ≤2 wt. %, *Cyperus rotundus* in an amount of ≤2 wt. %, *Swertia chirata* in an amount of ≤2 wt. %, *Curcuma longa* in an amount of ≤2 wt. %, *Aconitum heterophyllum* in an amount of ≤2 wt. %, *Berberis aristata* in an amount of ≤2 wt. %, *Plumbago zeylanica* in an amount of ≤2 wt. %, *Coriandrum sativum* in an amount of ≤2 wt. %, *Piper longum* in an amount of ≤2 wt. %, *Embelia ribes* in an amount of ≤2 wt. %, *Piper chaba* in an amount of ≤2 wt. %, *Zingiber officinale* in an amount of ≤2 wt. %, *Piper nigrum* in an amount of ≤2 wt. %, *Operculina turpethum* in an amount of ≤3 wt. %, *Baliospermum montanum* in an amount of ≤3 wt. %, *Cinnamomum tamala* in an amount of ≤3 wt. %, *Cinnamomum zeylanicum* in an amount of ≤2 wt. % and *Bamboo manna* in an amount of ≤3 wt. %, of the total weight of the composition.

Minerals

The embodiments of the composition disclosed herein include minerals such as Shilajit and Bhasmas. In an embodiment, the composition comprises of Shilajit. In another embodiment, the composition may further include at least one bhasma or calcined preparation selected from a group consisting of Swarna Makshika Bhasma, Loha Bhasma, and Kasisa Bhasma. Alternatively, the mineral element may also be selected from a group consisting of at least one of steel iron, swarna makshika (chalcopyrite) and green vitriol. However, it is also within the scope of claims provided herewith for the herbal composition to include, as a substitute or additionally, other similar calcined preparations or minerals without otherwise departing from the scope of the embodiments herein.

In an embodiment, the composition includes shilajit in an amount ranging from 5 to 8 wt. %. In another embodiment, the composition further includes at least one of Swarna Makshika Bhasma in an amount of ≤2 wt. %, Loha Bhasma in an amount of ≤2 wt. %, and Kasisa Bhasma in an amount of ≤2 wt. %, of the total weight of the composition.

Alkali

Further, the embodiments of the composition disclosed herein include alkali such as Yavakshara and Sarjikshara. In an embodiment, the composition includes at least one alkali selected from a group consisting of Yavakshara and Sarjikshara. Yavakshara disclosed in the various embodiments herein includes an alkali of *Hordeum vulgare*. Sarjikshara disclosed in the embodiments herein includes *Barilla*. In an embodiment, the composition disclosed herein includes at least one alkali in an amount of ≤2 wt %. In an embodiment, the alkali is at least one selected from a group consisting of Yavakshara in an amount of ≤2 wt % and Sarjikshara in an amount of ≤2 wt %, of the total weight of the composition.

Salt

The embodiments of the composition disclosed herein include salts such as Rock salt, Sonchal salt and Black salt. In an embodiment, the composition includes at least one salt selected from a group consisting of Rock salt, Sonchal salt and Black salt. In an embodiment, the composition comprises of at least one salt in an amount of ≤2 wt %. In an embodiment, the herbal composition disclosed herein includes at least one salt selected from a group consisting of Rock salt in an amount of ≤2 wt %, Sonchal salt in an amount of ≤2 wt % and Black salt in an amount of ≤2 wt %, of the total weight of the composition.

The disclosed composition, in the various embodiments herein, may further include one or more suitable excipient. The suitable excipients include solvents, binders, lubricants, herbal carriers, oils and salts that are generally known in the art. In an embodiment, the excipient includes *acacia* gum. The amount of gum *acacia* may be any amount suitable to perform the activity of an excipient. In an embodiment, the composition includes gum *acacia* in an amount in the range of 8 to 12 wt. % of the total composition.

Further, the amount of herb and mineral that may be included in the various embodiments of the disclosed composition may each be in the range of 0 to 15 wt %. In an embodiment, the composition includes *Saraca indica* (10 to 14 wt. %), *Symplocos racemosa* (8 to 12 wt. %), *Boerhavia diffusa* (8 to 12 wt. %), *Tinospora cordifolia* (2 to 5 wt. %), *Terminalia arjuna* (2 to 5 wt. %), *Saccharum officinarum* (2 to 5 wt. %), *Commiphora mukul* (5 to 8 wt. %), shilajit (5 to 8 wt. %), and at least one bhasma selected from a group consisting of Swarna Makshika Bhasma, Loha Bhasma, and Kasisa Bhasma.

In another embodiment, the composition includes *Saraca indica* (10 to 14 wt. %); *Symplocos racemosa* (8 to 12 wt. %); *Boerhavia diffusa* (8 to 12 wt. %); *Tinospora cordifolia* (2 to 5 wt. %); *Terminalia arjuna* (2 to 5 wt. %); *Saccharum officinarum* (2 to 5 wt. %); *Commiphora mukul* (5 to 8 wt. %); shilajit (5 to 8 wt. %); at least one bhasma selected from a group consisting of Swarna Makshika Bhasma (≤2 wt %), Loha Bhasma (≤2 wt %), and Kasisa Bhasma (≤2 wt %); and at least one alkali selected from the group consisting of Yavakshara (≤2 wt %) and Sarjikshara (≤2 wt %).

In another embodiment, the composition includes *Saraca indica* (10 to 14 wt. %); *Symplocos racemosa* (8 to 12 wt. %); *Boerhavia diffusa* (8 to 12 wt. %); *Tinospora cordifolia* (2 to 5 wt. %); *Terminalia arjuna* (2 to 5 wt. %); *Saccharum officinarum* (2 to 5 wt. %); *Commiphora mukul* (5 to 8 wt. %); shilajit (5 to 8 wt. %); at least one bhasma selected from a group consisting of Swarna Makshika Bhasma (≤2 wt %), Loha Bhasma (≤2 wt %), and Kasisa Bhasma (≤2 wt %); and at least one salt selected from the group consisting of Rock salt (≤2 wt %), Sonchal salt (≤2 wt %), and Black salt (≤2 wt %).

In another embodiment, the composition includes *Saraca indica* (10 to 14 wt. %), *Symplocos racemosa* (8 to 12 wt. %), *Boerhavia diffusa* (8 to 12 wt. %), *Tinospora cordifolia* (2 to 5 wt. %), *Terminalia arjuna* (2 to 5 wt. %), *Saccharum officinarum* (2 to 5 wt. %), *Commiphora mukul* (5 to 8 wt. %), shilajit (5 to 8 wt. %), Swarna Makshika Bhasma, Loha Bhasma (≤2 wt %), Kasisa Bhasma (≤2 wt %), Yavakshara (≤2 wt %), Sarjikshara (≤2 wt %), Rock salt (≤2 wt %), Sonchal salt (≤2 wt %) and Black salt (≤2 wt %).

In an embodiment, the composition further includes *Saraca indica* (10 to 14 wt. %), *Symplocos racemosa* (8 to 12 wt. %), *Boerhavia diffusa* (8 to 12 wt. %), *Tinospora cordifolia* (2 to 5 wt. %), *Terminalia arjuna* (2 to 5 wt. %), *Saccharum officinarum* (2 to 5 wt. %), *Commiphora mukul* (5 to 8 wt. %) *Emblica officinalis* (≤2 wt. %), *Terminalia chebula* (≤2 wt. %), *Terminalia bellerica* (≤2 wt. %), *Stereospermum suaveolens* (≤2 wt. %), *Premna mucronata* (≤2 wt. %), *Gmelina arborea* (≤2 wt. %), *Aegle marmelos* (≤2 wt. %), *Oroxylum indicum* (≤2 wt. %), *Desmodium gangeticum* (≤2 wt. %), *Uraria picta* (≤2 wt. %), *Solanum indicum* (≤2 wt. %), *Solanum xanthocarpum* (≤2 wt. %), *Tribulus terrestris* (≤2 wt. %), *Sida cordifolia* (≤2 wt. %), *Nardostachys jatamansi* (≤3 wt. %), *Acacia catechu* (≤3 wt. %), *Rubia cordifolia* (≤3 wt. %), *Hemidesmus indicus* (≤2 wt. %), *Cedrus deodara* (≤3 wt. %), *Withania somnifera* (≤2 wt. %), *Pueraria tuberosa* (≤2 wt. %), *Hydnocarpus laurifolia* (≤2 wt. %), *Ficus glomerata* (≤2 wt. %), *Dioscorea bulbifera* (≤2 wt. %), *Cinnamomum camphora* (≤2 wt. %), *Acorus calamus* (≤2 wt. %), *Cyperus rotundus* (≤2 wt. %), Swertia chirata (≤2 wt. %), Curcuma longa (≤2 wt. %), Aconitum heterophyllum (≤2 wt. %), Berberis aristata (≤2 wt. %), Plumbago zeylanica (≤2 wt. %), Coriandrum sativum (≤2 wt. %), Piper longum (≤2 wt. %), Embelia ribes (≤2 wt. %), Piper chaba (≤2 wt. %), Zingiber officinale (≤2 wt. %), Piper nigrum (≤2 wt. %), Operculina turpethum (≤3 wt. %), Baliospermum montanum (≤3 wt. %), Cinnamomum tamala (≤3 wt. %), Cinnamomum zeylanicum (≤2 wt. %), Bamboo manna (≤3 wt. %), shilajit (5 to 8 wt. %), Makshika Bhasma (≤2 wt. %), Loha Bhasma (≤2 wt. %), and Kasisa Bhasma (≤2 wt. %).

In an embodiment, the composition further includes Saraca indica (10 to 14 wt. %), Symplocos racemosa (8 to 12 wt. %), Boerhavia diffusa (8 to 12 wt. %), Tinospora cordifolia (2 to 5 wt. %), Terminalia arjuna (2 to 5 wt. %), Saccharum officinarum (2 to 5 wt. %), Commiphora mukul (5 to 8 wt. %) Emblica officinalis (≤2 wt. %), Terminalia chebula (≤2 wt. %), Terminalia bellerica (≤2 wt. %), Stereospermum suaveolens (≤2 wt. %), Premna mucronata (≤2 wt. %), Gmelina arborea (≤2 wt. %), Aegle marmelos (≤2 wt. %), Oroxylum indicum (≤2 wt. %), Desmodium gangeticum (≤2 wt. %), Uraria picta (≤2 wt. %), Solanum indicum (≤2 wt. %), Solanum xanthocarpum (≤2 wt. %), Tribulus terrestris (≤2 wt. %), Sida cordifolia (≤2 wt. %), Nardostachys jatamansi (≤3 wt. %), Acacia catechu (≤3 wt. %), Rubia cordifolia (≤3 wt. %), Hemidesmus indicus (≤2 wt. %), Cedrus deodara (≤3 wt. %), Withania somnifera (≤2 wt. %), Pueraria tuberosa (≤2 wt. %), Hydnocarpus laurifolia (≤2 wt. %), Ficus glomerata (≤2 wt. %), Dioscorea bulbifera (≤2 wt. %), Cinnamomum camphora (≤2 wt. %), Acorus calamus (≤2 wt. %), Cyperus rotundus (≤2 wt. %), Swertia chirata (≤2 wt. %), Curcuma longa (≤2 wt. %), Aconitum heterophyllum (≤2 wt. %), Berberis aristata (≤2 wt. %), Plumbago zeylanica (≤2 wt. %), Coriandrum sativum (≤2 wt. %), Piper longum (≤2 wt. %), Embelia ribes (≤2 wt. %), Piper chaba (≤2 wt. %), Zingiber officinale (≤2 wt. %), Piper nigrum (≤2 wt. %), Operculina turpethum (≤3 wt. %), Baliospermum montanum (≤3 wt. %), Cinnamomum tamala (≤3 wt. %), Cinnamomum zeylanicum (≤2 wt. %), Bamboo manna (≤3 wt. %), shilajit (5 to 8 wt. %), Makshika Bhasma (≤2 wt. %), Loha Bhasma (≤2 wt. %), Kasisa Bhasma (≤2 wt. %), Yavakshara (≤2 wt %) and Sarjikshara (≤2 wt %).

n an embodiment, the composition further includes Saraca indica (10 to 14 wt. %), Symplocos racemosa (8 to 12 wt. %), Boerhavia diffusa (8 to 12 wt. %), Tinospora cordifolia (2 to 5 wt. %), Terminalia arjuna (2 to 5 wt. %), Saccharum officinarum (2 to 5 wt. %), Commiphora mukul (5 to 8 wt. %) Emblica officinalis (≤2 wt. %), Terminalia chebula (≤2 wt. %), Terminalia bellerica (≤2 wt. %), Stereospermum suaveolens (≤2 wt. %), Premna mucronata (≤2 wt. %), Gmelina arborea (≤2 wt. %), Aegle marmelos (≤2 wt. %), Oroxylum indicum (≤2 wt. %), Desmodium gangeticum (≤2 wt. %), Uraria picta (≤2 wt. %), Solanum indicum (≤2 wt. %), Solanum xanthocarpum (≤2 wt. %), Tribulus terrestris (≤2 wt. %), Sida cordifolia (≤2 wt. %), Nardostachys jatamansi (≤3 wt. %), Acacia catechu (≤3 wt. %), Rubia cordifolia (≤3 wt. %), Hemidesmus indicus (≤2 wt. %), Cedrus deodara (≤3 wt. %), Withania somnifera (≤2 wt. %), Pueraria tuberosa (≤2 wt. %), Hydnocarpus laurifolia (≤2 wt. %), Ficus glomerata (≤2 wt. %), Dioscorea bulbifera (≤2 wt. %), Cinnamomum camphora (≤2 wt. %), Acorus calamus (≤2 wt. %), Cyperus rotundus (≤2 wt. %), Swertia chirata (≤2 wt. %), Curcuma longa (≤2 wt. %), Aconitum heterophyllum (≤2 wt. %), Berberis aristata (≤2 wt. %), Plumbago zeylanica (≤2 wt. %), Coriandrum sativum (≤2 wt. %), Piper longum (≤2 wt. %), Embelia ribes (≤2 wt. %), Piper chaba (≤2 wt. %), Zingiber officinale (≤2 wt. %), Piper nigrum (≤2 wt. %), Operculina turpethum (≤3 wt. %), Baliospermum montanum (≤3 wt. %), Cinnamomum tamala (≤3 wt. %), Cinnamomum zeylanicum (≤2 wt. %), Bamboo manna (≤3 wt. %), shilajit (5 to 8 wt. %), Makshika Bhasma (≤2 wt. %), Loha Bhasma (≤2 wt. %), and Kasisa Bhasma (≤2 wt. %), Rock salt (≤2 wt %), Sonchal salt (≤2 wt %) and Black salt (≤2 wt %).

In an embodiment, the composition further includes Saraca indica (10 to 14 wt. %), Symplocos racemosa (8 to 12 wt. %), Boerhavia diffusa (8 to 12 wt. %), Tinospora cordifolia (2 to 5 wt. %), Terminalia arjuna (2 to 5 wt. %), Saccharum officinarum (2 to 5 wt. %), Commiphora mukul (5 to 8 wt. %) Emblica officinalis (≤2 wt. %), Terminalia chebula (≤2 wt. %), Terminalia bellerica (≤2 wt. %), Stereospermum suaveolens (≤2 wt. %), Premna mucronata (≤2 wt. %), Gmelina arborea (≤2 wt. %), Aegle marmelos (≤2 wt. %), Oroxylum indicum (≤2 wt. %), Desmodium gangeticum (≤2 wt. %), Uraria picta (≤2 wt. %), Solanum indicum (≤2 wt. %), Solanum xanthocarpum (≤2 wt. %), Tribulus terrestris (≤2 wt. %), Sida cordifolia (≤2 wt. %), Nardostachys jatamansi (≤3 wt. %), Acacia catechu (≤3 wt. %), Rubia cordifolia (≤3 wt. %), Hemidesmus indicus (≤2 wt. %), Cedrus deodara (≤3 wt. %), Withania somnifera (≤2 wt. %), Pueraria tuberosa (≤2 wt. %), Hydnocarpus laurifolia (≤2 wt. %), Ficus glomerata (≤2 wt. %), Dioscorea bulbifera (≤2 wt. %), Cinnamomum camphora (≤2 wt. %), Acorus calamus (≤2 wt. %), Cyperus rotundus (≤2 wt. %), Swertia chirata (≤2 wt. %), Curcuma longa (≤2 wt. %), Aconitum heterophyllum (≤2 wt. %), Berberis aristata (≤2 wt. %), Plumbago zeylanica (≤2 wt. %), Coriandrum sativum (≤2 wt. %), Piper longum (≤2 wt. %), Embelia ribes (≤2 wt. %), Piper chaba (≤2 wt. %), Zingiber officinale (≤2 wt. %), Piper nigrum (≤2 wt. %), Operculina turpethum (≤3 wt. %), Baliospermum montanum (≤3 wt. %), Cinnamomum tamala (≤3 wt. %), Cinnamomum zeylanicum (≤2 wt. %), Bamboo manna (≤3 wt. %), shilajit (5 to 8 wt. %), Makshika Bhasma (≤2 wt. %), Loha Bhasma (≤2 wt. %), and Kasisa Bhasma (≤2 wt. %), Yavakshara (≤2 wt %), Sarjikshara (≤2 wt %), Rock salt (≤2 wt %), Sonchal salt (≤2 wt %) and Black salt (≤2 wt %), of the total weight of the composition. All weight percentages are based on the total weight of the composition. However, it is apparent that slight variations and modifications in the amount of the ingredients may be practiced without otherwise departing from the intended function of the disclosed composition.

The herbal composition disclosed herein is best suited for oral administration and may be formulated accordingly into various suitable dosage forms. The herbal composition may be in the form of tablets, pellets, lozenges, granules, capsules, solutions, pellets, emulsions, suspensions, or any other form suitable for use. Generally known methods of formulating/processing ayurvedic compositions may be used to formulate the desired dosage forms. In an embodiment, the disclosed composition is formulated in the form of tablets, preferably 500 mg tablets. Table 1 is an exemplary embodiment depicting the quantities of each ingredient in a 500 mg tablet. Accordingly, embodiments disclosed herein include a tablet for treating PCOS and PCOS associated symptoms. In an embodiment, the tablet is a 500 mg tablet comprising ingredients as depicted in Table 1.

TABLE 1

Each 500 mg tablet includes:

| No. | Sanskrit Name | Part used | Latin/English name | Quantity |
|-----|---------------|-----------|--------------------|----------|
| 1 | Ashoka | Dried heartwood | *Saraca indica* | 60 mg |
| 2 | Lodhra | Dried stem bark | *Symplocos racemosa* | 50 mg |
| 3 | Punarnava | Dry root | *Boerhavia diffusa* | 50 mg |
| 4 | Guduchi | Dry stem | *Tinospora cordifolia* | 16 mg |
| 5 | Amalaki | dry fruits | *Emblica officinalis* | 4 mg |
| 6 | Hareetaki | dry fruits | *Terminalia chebula* | 2 mg |
| 7 | Vibhitaki | dry fruits | *Terminalia bellerica* | 2 mg |
| 8 | Patala | dry root | *Stereospermum suaveolens* | 2 mg |
| 9 | Agnimantha | dry root | *Premna mucronata* | 2 mg |
| 10 | Gambhari | dry root | *Gmelina arborea* | 2 mg |
| 11 | Bilva | dry root | *Aegle marmelos* | 4 mg |
| 12 | Shyonaka | dry root | *Oroxylum indicum* | 2 mg |
| 13 | Shalaparni | dry plant | *Desmodium gangeticum* | 2 mg |
| 14 | Prshniparni | dry plant | *Uraria picta* | 2 mg |
| 15 | Brhati | dry plant | *Solanum indicum* | 2 mg |
| 16 | Kantakari | dry plant | *Solanum xanthocarpum* | 2 mg |
| 17 | Gokshura | dry fruit | *Tribulus terrestris* | 2 mg |
| 18 | Bala | Dry root | *Sida cordifolia* | 2 mg |
| 19 | Jatamansi | Dried rhizome | *Nardostachys jatamansi* | 8 mg |
| 20 | Khadira | Dried heartwood | *Acacia catechu* | 8 mg |
| 21 | Manjishtha | Dried root | *Rubia cordifolia* | 6 mg |
| 22 | Sariva | Dried root | *Hemidesmus indicus* | 2 mg |
| 23 | Devadaru | Dried heartwood | *Cedrus deodara* | 8 mg |
| 24 | Arjuna | Dried stem bark | *Terminalia arjuna* | 16 mg |
| 25 | Ashvagandha | Dried root | *Withania somnifera* | 4 mg |
| 26 | Vidari | Dried tuber | *Pueraria tuberosa* | 4 mg |
| 27 | Bilva | dry fruit pulp | *Aegle marmelos* | 4 mg |
| 28 | Tuvaraka | Dried seeds | *Hydnocarpus laurifolia* | 4 mg |
| 29 | Udumbara | Dried stem bark | *Ficus glomerate* | 4 mg |
| 30 | Varahi | Dried tuber | *Dioscorea bulbifera* | 4 mg |
| 31 | Karpura | Sublimate crystals | *Cinnamomum camphora* | 2 mg |
| 32 | Vacha | Dried rhizome | *Acorus calamus* | 2 mg |
| 33 | Musta | Dried root | *Cyperus rotundas* | 2 mg |
| 34 | Kirata | Dried whole plant | *Swertia chirata* | 2 mg |
| 35 | Guduchi | Starchy extract of fresh stem | *Tinospora cordifolia* | 2 mg |
| 36 | Haridra | Dried rhizome | *Curcuma longa* | 2 mg |
| 37 | Ativisha | Dried root | *Aconitum heterophyllum* | 2 mg |
| 38 | Daruharidra | Dried root | *Berberis aristata* | 2 mg |
| 39 | Pippalimula | Dried root | *Piper longum* | 2 mg |
| 40 | Chitraka | Dried root | *Plumbago zeylanica* | 2 mg |
| 41 | Chavya | Dried stem | *Piper chaba* | 2 mg |
| 42 | Dhanyaka | Dried fruit | *Coriandrum sativum* | 2 mg |
| 43 | Vidanga | Dried fruit | *Embelia ribes* | 2 mg |
| 44 | Gajapippali | dry root | *Piper chaba* | 2 mg |
| 45 | Shunthi | Dry rhizome | *Zingiber officinale* | 2 mg |
| 46 | Maricha | Dry fruits | *Piper nigrum* | 2 mg |
| 47 | Pippali | dry fruits | *Piper longum* | 2 mg |
| 48 | Trivrit | Dried root | *Operculina turpethum* | 8 mg |
| 49 | Danti | Dried root | *Baliospermum montanum* | 8 mg |
| 50 | Patra | Dry leaves | *Cinnamomum tamala* | 8 mg |
| 51 | Tvak | Dry stem bark | *Cinnamomum zeylanica* | 8 mg |
| 52 | Vamshalochana | Dried secretion | Bamboo manna | 8 mg |
| 53 | Sita | Extract-rock sugar | *Saccharum officinarum-* | 16 mg |
| 54 | Guggulu | Oleo-gum-resin | *Commiphora mukul* | 32 mg |
| 55 | Shilajit | Fossil resin | *Asphaltum punjabianum* | 32 mg |
| 56 | Yavakshara | alkali | Alkali of *Hordeum vulgare* | 2 mg |
| 57 | Sarjikshara | alkali | Barilla | 2 mg |
| 58 | Saindhava | salt | Rock salt | 2 mg |
| 59 | Souvarchala Lavana | salt | Sonchal salt | 2 mg |
| 60 | Vida Lavana | salt | Black salt | 2 mg |
| 61 | Swarnamakshika bhasma | Incinerated ore | Incinerated copper pyrite | 2 mg |
| 62 | Loha Bhasma | Incinerated metal | Calx of iron | 2 mg |
| 63 | Kasisa Bhasma | Incinerated green vitriol | Calx of green vitriol (ferrous sulphate) | 2 mg |
| 64 | Excipient | Resin | Gum acacia | 50 mg |

Embodiments of the disclosed formulation in tablet form were analyzed for parameters including physicochemical properties such as Tablet hardness, Loss on drying, Assay, Disintegration time, Ash value, etc and the results were noted. Table 2 depicts the results of the analysis performed to determine the physicochemical properties of an embodiment of the disclosed formulation. In an embodiment, the disclosed formulation tablets have the characteristics as depicted in Table 2. It will be apparent to those skilled in the art that many modifications, both to materials and methods, may be practiced without departing from the scope of the claims herein.

TABLE 2

| TEST PARAMETERS | SPECIFICATIONS |
| --- | --- |
| Description | Blackish brown biconvex shaped tablets |
| Qualitative identification | Tests positive for. iron, sodium, chloride, tannins, flavonoids, glycosides and alkaloids |
| Average weight | 500 mg ± 12.5 mg |
| Uniformity of weight | ±2.5% of actual average weight |
| Average tablet hardness | 4.0 kg/cm$^2$ |
| Loss on drying | 2.5-3.5% w/w |
| Methanol soluble extractive | Not less than 25% w/v |
| Water soluble extractive | Not less than 35% w/v |
| Ash value | 18.0% w/w |
| Average Disintegration time | 15-20 minutes |

Method

Disclosed herein are embodiments of a method of preparing the herbal composition. In an embodiment, the method includes, preparing a grinding decoction;

levigating a mixture of powdered herbs and bhasmas with grinding juice in a grinder;

adding Guggulu (resin of *Commiphora mukul*) and Shilajit into said grinder and grinding with a first portion of said grinding decoction, to obtain a homogenous ground mass.

In an embodiment, at least one alkali selected from Yavakshara and Sarjikshara is added along with the powdered herbs to said grinder. Yavakshara alkali (Alkali of *Hordeum vulgare*) and Sarjikshara alkali (*Barilla*) may be prepared by methods generally known in the field. For example: Acharya Sadananda Sharma, Rasatarangini, Pandit Kashinath Shastri, Tarang 13/3-5, Chaukhambha Sanskrit Bhavan, Varanasi, Reprint, 2014; and Acharya Sadananda Sharma, Rasatarangini, Pandit Kashinath Shastri, Tarang 13/45-47, Chaukhambha Sanskrit Bhavan, Varanasi, Reprint, 2014. In another embodiment, at least one salt selected from rock salt, sonchal salt and black salt is added along with the powdered herbs to said grinder.

In an embodiment, the method of preparation further includes mixing the obtained composition with a suitable excipient and grinding to obtain a semisolid mass. The obtained semisolid mass may further be processed by methods known in the field to obtain oral dosage forms. In an embodiment, the method of preparation further includes drying at 55 to 65 degrees Celsius, granulating and punching to obtain tablets. In an embodiment, the method includes drying the obtained mass at a temperature of 60 degrees Celsius in a hot air oven, granulating by wet granulation and punching to obtain 500 mg tablets. Granulation and tablet punching may be performed according to methods generally known in the field. FIG. 1 depicts a flowchart for the preparation of fortified tablets. All raw materials such as herbs and minerals instrumental in the various embodiments herein are of genuine purity whose identity and quality are confirmed by traditional experts and are as per generally acceptable standards. The raw materials instrumental in the various embodiments herein are subjected to appropriate cleaning procedures that are considered standard and acceptable in the field. In an embodiment, the raw materials were subjected to cleaning with potable mineral water prior to its use.

Preparation of grinding decoction: In the various embodiments disclosed herein, the grinding decoction is a decoction of herbs that facilitates grinding. The grinding decoction provides lubrication and improves binding of the ingredients. In an embodiment, the grinding decoction includes a decoction of at least one ingredient selected from a group consisting of *Emblica officinalis, Terminalia chebula, Terminalia bellerica, Stereospermum suaveolens, Premna mucronate, Gmelina arborea, Aegle marmelos, Oroxylum indicum, Desmodium gangeticum, Uraria picta, Solanum indicum, Solanum xanthocarpum, Tribulus terrestris, Asparagus racemosus, Cyperus rotundus, Vitis vinifera, Piper longum, Oldenlandia umbellata, Mimosa pudica, Areca catechu* and *Citrus medica* are used to prepare the grinding decoction.

The herb ingredients used in the preparation of grinding decoction may be included as a whole or in parts such as leaves, roots, stem, fruits, seeds, etc. The ingredients that are used may comprise of herbs in dry or fresh form. In an embodiment, said herb ingredients include coarsely powdered form of herbs that is sieved through a 10-mesh screen. In an embodiment, the ingredients include coarsely powdered form of the following ingredients: dry fruits of *Emblica officinalis*, dry fruits of *Terminalia chebula*, dry fruits of *Terminalia bellerica*, dry roots of *Stereospermum suaveolens*, dry roots of *Premna mucronate*, dry roots of *Gmelina arborea*, dry roots of *Aegle marmelos*, dry roots of *Oroxylum indicum*, dry plants of *Desmodium gangeticum*, dry plants of *Uraria picta*, dry roots of *Solanum indicum*, dry plants of *Solanum xanthocarpum*, dry fruits of *Tribulus terrestris*, fresh roots of *Asparagus racemosus*, dry roots of *Cyperus rotundus*, dry fruits of *Vitis vinifera*, dry fruits of *Piper longum*, dry whole plant of *Oldenlandia umbellata*, dry whole plant of *Mimosa pudica*, fresh tender leaves of *Areca catechu* and dry seeds of *Citrus medica*.

In an embodiment, the grinding decoction includes ingredients as depicted in Table 3. Table 3 depicts the Grinding ingredients required for Grinding decoction.

TABLE 3

Decoction of following herbs:

| | | | |
| --- | --- | --- | --- |
| 1 | Amalaki dry fruits | *Emblica officinalis* | 1 part |
| 2 | Hareetaki dry fruits | *Terminalia chebula* | 1 part |
| 3 | Vibhitaki dry fruits | *Terminalia bellerica* | 1 part |
| 4 | Patala dry root | *Stereospermum suaveolens* | ½ part |
| 5 | Agnimantha dry root | *Premna mucronata* | ½ part |
| 6 | Gambhari dry root | *Gmelina arborea* | ½ part |
| 7 | Bilva dry root | *Aegle marmelos* | ½ part |
| 8 | Shyonaka dry root | *Oroxylum indicum* | ½ part |
| 9 | Shalaparni dry plant | *Desmodium gangeticum* | ½ part |
| 10 | Prshniparni dry plant | *Uraria picta* | ½ part |
| 11 | Brhati dry root | *Solanum indicum* | ½ part |
| 12 | Kantakari dry plant | *Solanum xanthocarpum* | ½ part |
| 13 | Gokshura dry fruit | *Tribulus terrestris* | ½ part |
| 14 | Shatavari fresh root | *Asparagus racemosus* | 4 parts |
| 15 | Musta dried root | *Cyperus rotundas* | 1 part |
| 16 | Draksha dried fruit | *Vitis vinifera* | 1 part |
| 17 | Pippali dry fruits | *Piper longum* | 1 part |
| 18 | Parpata dried whole plant | *Oldanlandia umbelata* | 1 part |
| 19 | Lajjalu dried whole plant | *Mimosa pudica* | 1 part |
| 20 | Puga fresh tender leaves | *Areca catechu* | 1 part |
| 21 | Madiphala dried seeds | *Citrus medica* | 1 part |
| 22 | Jala | Water | 304 parts (i.e. 16 times of total drugs) |
| | Avashesha (Reduced to) | | ⅛ part of water |

The decoction may be prepared by any method of decocting generally known in the field. In an embodiment, the method of preparation of grinding decoction includes, soaking the grinding ingredients in water; and boiling to obtain a decoction.

In an embodiment, soaking may be performed by soaking the grinding herbs in 16 parts of water for a period of 5 to 15 hours or overnight. In one embodiment, boiling is performed at a high temperature of 80 to 85 degree Celsius, until amount of liquid is reduced to $\frac{1}{8}^{th}$ of the initial volume. The grinding decoction may be filtered before use. The grinding decoction may further be apportioned into two or three portions as per requirement. The first portion of the grinding decoction may be used to grind the levigated mixture. Gum *acacia* may be added into the composition by dissolving in a second portion of the grinding decoction which may be added to the obtained homogenous mass. Alternatively, Gum *acacia* may be dissolved in the first portion of grinding decoction and added to the powdered herbs while grinding. It would be apparent to a person skilled in the art that the portion size, number, etc are aspects which are flexible and may vary depending on requirement.

Grinding Juice: In an embodiment, the grinding juice is fresh juice of herbs comprising at least one herb selected from a group consisting of *Punica granatum, Cynodon dactylon, Aloe vera, Piper betle* and *Coccinia indica*. In an embodiment, levigation is performed by grinding the blend of bhasmas and herb ingredients for a period of about 1 to 3 hours in each of the following fresh juice of herbs added one by one: fresh fruit juice of *Punica granatum*, fresh plant juice of *Cynodon dactylon*, fresh leaf juice of *Aloe vera*, fresh leaf juice of *Piper betle* and fresh leaf juice of *Coccinia indica*. Table 4 illustrates the list of herbs that are used in levigating.

TABLE 4

Fresh juice of herbs for levigation
Fresh juice of following herbs:

| | | | |
|---|---|---|---|
| 1. | Dadima fresh fruit juice | *Punica granatum* | 1 part |
| 2. | Durva fresh plant juice | *Cynodon dactylon* | 1 part |
| 3. | Kumari fresh leaf juice | *Aloe vera* | 1 part |
| 4. | Tambula fresh leaf juice | *Piper betle* | 1 part |
| 5. | Bimbi fresh leaf juice | *Coccinia indica* | 1 part |

Levigation: In the various embodiments disclosed herein, levigation of said mixture comprising bhasma(s), and powdered herbs may be performed by methods generally known in the field. In an embodiment, levigation is performed to obtain a levigated mixture, by grinding the blend of bhasmas and herb ingredients for a period of about 1 to 3 hours in each of the following fresh juice of herbs added one by one: fresh fruit juice of *Punica granatum*, fresh plant juice of *Cynodon dactylon*, fresh leaf juice of *Aloe vera*, fresh leaf juice of *Piper betle* and fresh leaf juice of *Coccinia indica*.

The herbs that are mixed include finely powdered herbs that are instrumental in the composition as disclosed in the various embodiments herein. In an embodiment, said herbs include heartwood of *Saraca indica*, stem bark of *Symplocos racemosa*, root of *Boerhavia diffusa*, stem of *Tinospora cordifolia*, stem bark of *Terminalia arjuna* and extract of *Saccharum officinarum*. In another embodiment, said herbs include fruits of *Emblica officinalis*, fruits of *Terminalia chebula*, fruits of *Terminalia bellerica*, roots of *Stereospermum suaveolens*, roots of *Premna mucronata*, roots of *Gmelina arborea*, roots and fruit pulp of *Aegle marmelos*, roots of *Oroxylum indicum*, whole plant of *Desmodium gangeticum*, whole plant of *Uraria picta*, whole plant of *Solanum indicum*, whole plant of *Solanum xanthocarpum*, fruits of *Tribulus terrestris*, roots of *Sida cordifolia*, rhizome of *Nardostachys jatamansi*, heartwood of *Acacia catechu*, roots of *Rubia cordifolia*, roots of *Hemidesmus indicus*, heartwood of *Cedrus deodara*, roots of *Withania somnifera*, tuber of *Pueraria tuberosa*, seeds of *Hydnocarpus laurifolia*, stem bark of *Ficus glomerata*, tuber of *Dioscorea bulbifera*, sublimate crystals of *Cinnamomum camphora*, rhizome of *Acorus calamus*, roots of *Cyperus rotundus*, whole plant of *Swertia chirata*, rhizome of *Curcuma longa*, roots of *Aconitum heterophyllum*, roots of *Berberis aristata*, roots of *Plumbago zeylanica*, fruits of *Coriandrum sativum*, fruits and roots of *Piper longum*, roots and stem of *Piper chaba*, rhizome of *Zingiber officinale*, fruits of *Piper nigrum*, fruits of *Embelia ribes*, roots of *Operculina turpethum*, roots of *Baliospermum montanum*, leaves of *Cinnamomum tamala*, stem bark of *Cinnamomum zeylanicum* and secretion of *Bamboo manna*.

The bhasmas that are used in the various embodiments of the disclosed herbal composition may be prepared by methods that are generally known in the field. The bhasmas may be prepared by a process comprising of the steps of Shodhana or Purification; Trituration; and Marana or Incineration. In an embodiment, the process for preparation of Bhasmas includes:

selecting a mineral;
purifying the mineral;
triturating the purified mineral; and
incinerating to obtain bhasma.

Selection of a mineral: In an embodiment, said mineral is genuine standard mineral such as steel iron, swarna makshika (chalcopyrite), iron rust, zinc, tin, hart's horn, coral, pearl oyster, silver foil or mica, whose identity and quality has been confirmed by in-house traditional experts. In an embodiment, the selected mineral is further cleaned with potable mineral water; and dried at a temperature of about 50 degree Celsius. Drying of the mineral in the various embodiments herein may be achieved by drying in a hot air oven at a temperature of about 50 degree Celsius; or by exposure to sunlight.

Purification of mineral: The purification (also referred to as Shodhana) of the mineral may be performed by generally known methods in the field such as triturating, quenching, boiling, etc. In an embodiment, said purification of mineral includes general purification (also referred to as Samanya shodhana) and Special purification (also referred to as Vishesha shodhana). In another embodiment, purification may be a single step process involving boiling, quenching and/or trituration.

Trituration of purified mineral: Trituration of the mineral may be performed by generally known methods in the field. In an embodiment, trituration is performed by grinding the mineral with herbal decoction. In another embodiment, trituration is performed by grinding the mineral with herbal juice. The herbal decoction or herbal juice used for triturating include any herbal decoction/juice that is generally used for triturating in the preparation of bhasmas such as Triphala, Lemon juice, *Aloe vera* juice etc. In an embodiment, trituration is performed by grinding the mineral with Gomutra (cow's urine). Trituration may be performed until a homogenous mixture having reduced particle size is obtained.

Incineration: Incineration of the mineral may be performed by methods generally known in the field. In an embodiment, incineration is performed by putta system. In an embodiment, said incineration of mineral includes preparing discs of the mineral; and subjecting said discs to a specific quantum and pattern of heat to obtain incinerated mineral powder or bhasma. In an embodiment, said discs have a thickness of about 0.5 cm thickness and a diameter of about 2.5 cm. The prepared discs may further be dried at a temperature of about 50 degree Celsius. The discs may be exposed to sunlight or exposed to a temperature of about 50 degrees Celsius in a hot air oven. The discs of mineral are further subjected to heat by sealing inside a capsule made using earthern saucers also known as the puta system of heating which includes preparation of Sharava Samputa and heating in Gaja puta, Ardha Gaja puta, Kukkuta puta, Laghu puta, etc. The incinerated mineral powder is further powdered and used as bhasma. In an embodiment, the incinerated mineral powder may again be subjected to repeated rounds of trituration and incineration in order to obtain a Bhasma. The procedure may be repeated for about 7 to 30 times in order to obtain Bhasma.

Figure 2:
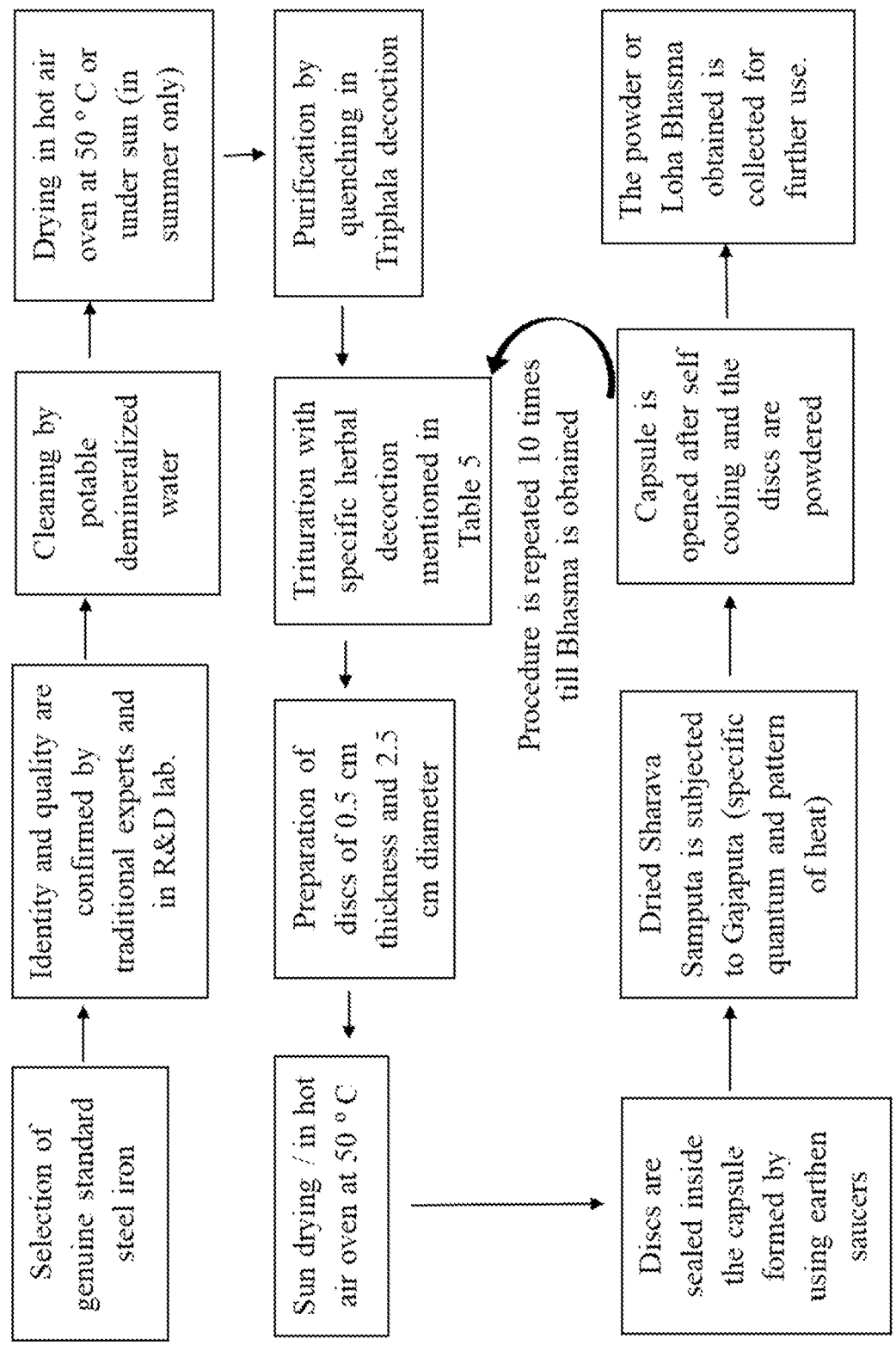
FIG. 2 depicts a flowchart for the preparation of Loha Bhasma, according to embodiments as disclosed herein.

Loha Bhasma: Loha bhasma may be prepared by methods generally known in the field. The mineral or starting material used in the preparation of Loha bhasma in the various embodiments herein include Steel iron, (also referred to as "Loha"). The starting material is further purified, triturated and incinerated to obtain Loha Bhasma. The process of preparation of Loha bhasma includes cleaning and drying the mineral, purifying said mineral, triturating with herbal decoction and/or herbal juices, and incinerating by putta system to obtain a powder or bhasma. The obtained powder is subjected to the putta system of incineration by generally known methods. The trituration and incineration process of the obtained powder may further be repeated in many cycles to obtain Loha Bhasma. In an embodiment, the obtained powder is triturated and incinerated for 30 cycles in order to obtain Loha Bhasma. In an embodiment, said purification process of the mineral includes quenching the mineral in Triphala decoction. The herbal decoction/juice used in the trituration process of Loha bhasma includes a decoction of at least one of the following ingredients: *Emblica officinalis, Terminalia* chebula, *Terminalia bellerica, Crataeva nurvala, Boerhavia diffusa, Bauhinia variegata, Eclipta alba, Asparagus racemosus*, and Cow urine. Table 5 depicts the ingredients of the herbal decoction used in the preparation of Loha bhasma. FIG. 2 depicts a flowchart for the preparation of Loha Bhasma.

TABLE 5

Herbal decoction used for trituration while preparing Loha Bhasma.
Decoction of following herbs:

| 1 | Amalaki | *Emblica officinalis* | 1 part |
| 2 | Hareetaki | *Terminalia chebula* | 1 part |
| 3 | Vibheetaki | *Terminalia bellerica* | 1 part |
| 4 | Varuna | *Crataeva nurvala* | 1 part |
| 5 | Punarnava | *Boerhavia diffusa* | 1 part |
| 6 | Kanchanara | *Bauhinia variegata* | 1 part |
| 7 | Bhringaraja | *Eclipta alba* | 1 part |
| 8 | Shatavari | *Asparagus racemosus* | 1 part |
| 9 | Gomutra | Cow urine | 64 parts |
| 10 | Jala | Water | 64 parts |
|  | Avashesha (Reduced to) |  | ⅛ part of liquid |

Figure 3:
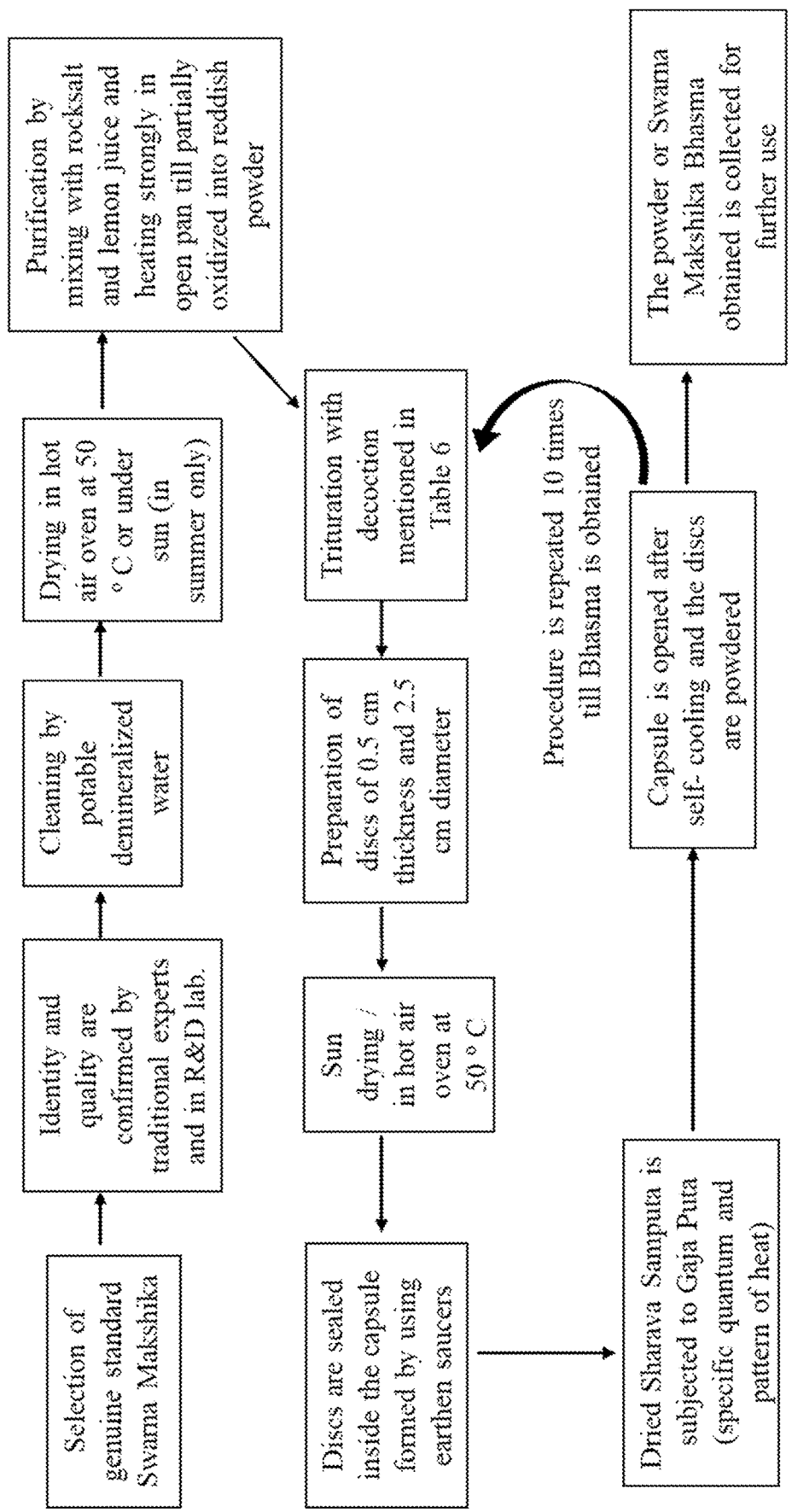
FIG. 3 depicts a flowchart for the preparation of Swarna makshika Bhasma, according to embodiments as disclosed herein.

Swarna Makshika Bhasma: Swarna makshika bhasma may be prepared by methods generally known in the field. The mineral or starting material used in the preparation of Swarna makshika bhasma in the various embodiments herein include Copper pyrite, (also referred to as "Swarna makshika"). The starting material is purified, triturated and incinerated to obtain a Bhasma. In an embodiment, the process of preparation of Swarna makshika bhasma includes cleaning and drying the mineral, purifying said mineral, triturating with herbal decoction and/or herbal juices, and incinerating by putta system to obtain a powder or bhasma. The obtained powder is subjected to the putta system of incineration by generally known methods. The trituration and incineration process of the obtained powder may further be repeated in many cycles to obtain Swarna makshika Bhasma. In an embodiment, the obtained powder is triturated and incinerated for 10 cycles in order to obtain Swarna makshika Bhasma. In an embodiment, said purification process of the mineral includes mixing the mineral with rock salt and lemon juice, and heating. In an embodiment, said heating is performed in an open pan until the mixture is partially oxidized and turns into a reddish colored powder. The herbal decoction/juice used in the trituration process of Swarna makshika bhasma includes a decoction of at least one of the following ingredients: *Emblica officinalis, Terminalia chebula, Terminalia bellerica, Cyperus rotundus, Ficus benghalensis, Curcuma longa* and *Rubia cordifolia*. Table 6 depicts the ingredients of the herbal decoction used in the preparation of Swarna makshika bhasma. FIG. 3 depicts a flowchart for the preparation of Swarna makshika Bhasma.

TABLE 6

Ingredients for Herbal decoction used for trituration
while preparing Swarna makshika Bhasma.
Decoction of following herbs:

| 1 | Amalaki dried fruit | *Emblica officinalis* | 1 part |
| 2 | Hareetaki dried fruit | *Terminalia chebula* | 1 part |
| 3 | Vibheetaki dried fruit | *Terminalia bellerica* | 1 part |
| 4 | Musta dried rhizome | *Cyperus rotundus* | 1 part |
| 5 | Vata dried root bark | *Ficus benghalensis* | 1 part |
| 6 | Haridra dried rhizome | *Curcuma longa* | 1 part |
| 7 | Manjishtha dried root | *Rubia cordifolia* | 1 part |
| 8 | Jala | Water | 112 parts |
|  | Avashesha (Reduced to) |  | ⅛ part of liquid |

Figure 4:
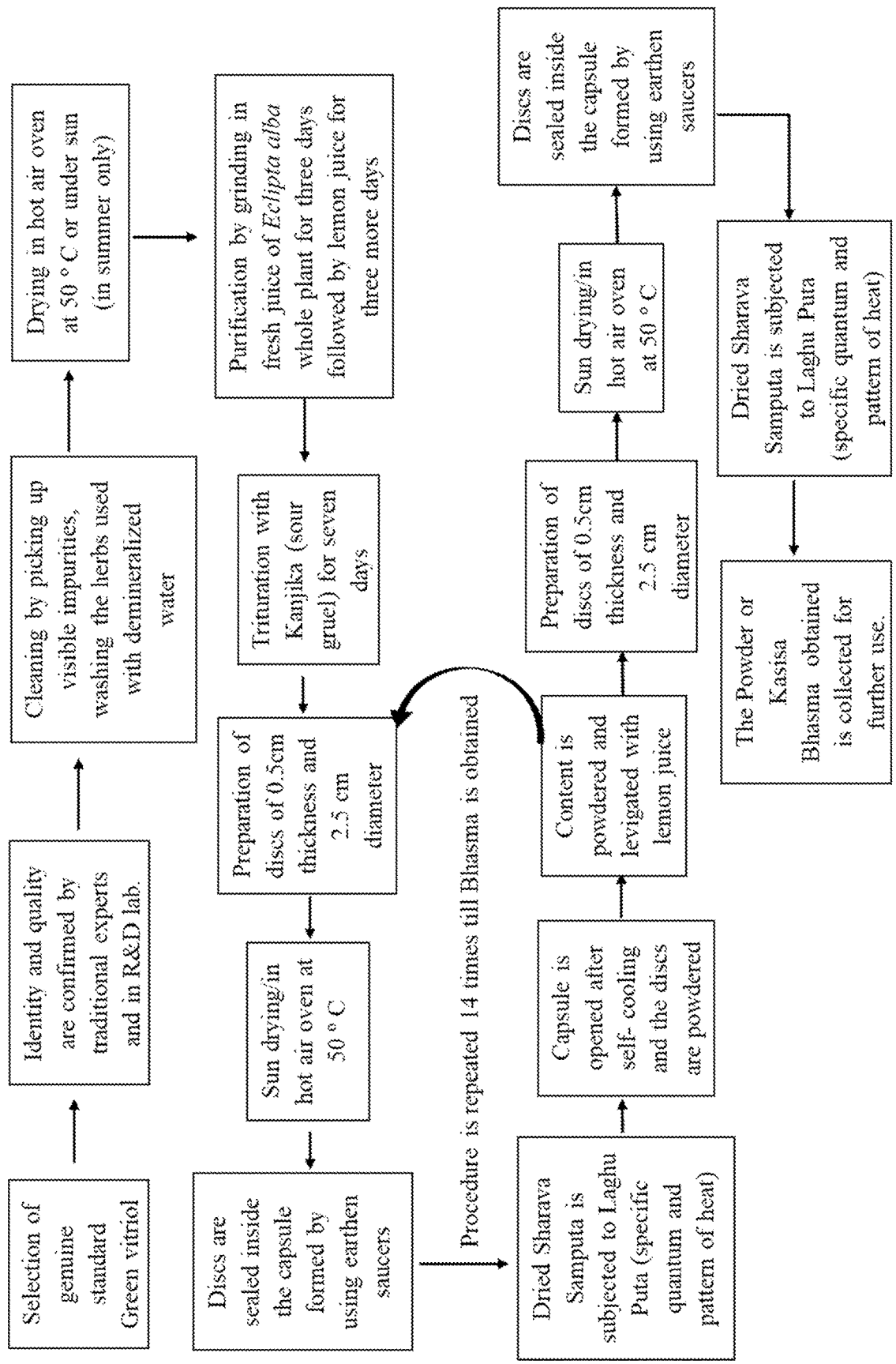
FIG. 4 depicts a flowchart for the preparation of Kasisa Bhasma, according to embodiments as disclosed herein.

Kasisa Bhasma: Kasisa bhasma may be prepared by methods generally known in the field. The mineral or starting material used in the preparation of Kasisa bhasma in the various embodiments herein include green vitriol. The starting material is purified, triturated and incinerated to obtain a Bhasma. In an embodiment, purification may be by grinding in fresh juice of *Eclipta alba* (whole plant) for three days followed by grinding in lemon juice for three more days. In an embodiment, the herbal decoction/juice used for trituration in the preparation of Kasisa bhasma includes Kanjika (sour gruel). Sour gruel may be prepared by any method generally known in the field. For example: 1 part of washed Shastika Rice (*Oryza sativum*, a special variety of rice which takes 60 days to harvest) and 14 parts of water were taken and put in a stainless-steel container and kept on low flame till it was cooked. Supernatant liquid is called as Manda. This Manda is poured into a porcelain jar, with three parts of boiled and cooled water and stirred well. Jar is closed, sealed left undisturbed for appropriate fermentation. Kanjika a sour fermented gruel is collected after 4 weeks. FIG. 4 depicts a flowchart for preparation of Kasisa Bhasma.

The starting material is purified, triturated and incinerated to obtain a Bhasma. In an embodiment, the process of preparation of Kasisa bhasma includes cleaning and drying the mineral, purifying said mineral, triturating with herbal decoction and/or herbal juices, and incinerating by putta system to obtain a powder or bhasma. The obtained powder is subjected to the putta system of incineration by generally known methods. The trituration and incineration process of the obtained powder may further be repeated in many cycles to obtain Bhasma. In an embodiment, the obtained powder is triturated and incinerated for 14 cycles in order to obtain Kassisa Bhasma. In an embodiment, the purification process of the mineral includes levigating the mineral with juice of *Eclipta alba* for about 3 days, followed by levigation with lemon juice for about 3 days. It is then dried under sun or in hot air oven at 50 degree Celsius to obtain a powder. The purified powder is then subjected to grinding in Kanjika for about seven days. The dough obtained is incinerated by subjecting it to heat using laghu putta. The obtained powder/disc is further triturated with lemon juice and incinerated again. The cycle of trituration and incineration is performed 14 times to obtain bhasma.

Adding Guggulu (resin of *Commiphora mukul*) and Shilajit into said grinder and grinding: In various embodiments disclosed herein, the step of adding of Guggulu (resin of *Commiphora mukul*) and Shilajit includes adding herbs to the levigated mixture and grinding with a first portion of the grinding decoction, to obtain a homogenous mixture. In an embodiment, said grinding is performed in a grinder such that a homogenous mass is obtained.

In an embodiment, the grinding decoction is added, subsequent to the addition of Guggulu (resin of *Commiphora mukul*) and Shilajit, in small quantities at frequent intervals. Once the grinding decoction is added grinding is continued for 65-75 hours at about 100-120 rpm. In an embodiment, grinding is continued for 72 hours at about 120 rpm, to obtain a homogenous mass. In an embodiment, the method of preparation further includes adding excipient to the homogenous mass, wherein gum *acacia* is added by dissolving in a second portion of grinding decoction. Grinding may further be continued once the excipient is added for a period of 1 to 4 hours to obtain a semisolid mass. In an embodiment, grinding is continued for a period of 3 hours.

Treatment

Disclosed herein are embodiments of a method for treatment and management of PCOS. The embodiments disclosed herein are instrumental in treatment and management of PCOS associated symptoms such as irregular menstrual cycle, hirsutism, alopecia, acne, obesity, hypertension, amenorrhea, etc. Further embodiments of the method disclosed herein may also be used to treat gynecological disorders such as female infertility, dysmenorrhoea, leucorrhoea, excess menstrual bleeding as seen in Dysfunctional Uterine Bleeding, etc. Furthermore, the embodiments disclosed herein may also be instrumental in improving reproductive health of a patient.

In an embodiment, the method includes administering to a patient a therapeutically effective amount of the composition as disclosed in various embodiments herein. The patient may include any individual in need of such treatment including ones having/suspected of having PCOS or associated symptoms such as irregular menstrual cycle, hirsutism, alopecia, acne, obesity, hypertension, amenorrhea, etc. Further, the patient may also include any individual having gynecological complications such as infertility, dysmenorrhoea, leucorrhoea, excess menstrual bleeding as seen in Dysfunctional Uterine Bleeding, etc. The patient may further include any individual intending to improving reproductive health. Further disclosed are embodiments of a method for manufacturing a medicament. In an embodiment, the method for manufacturing a medicament comprises combining a suitable excipient and the disclosed composition. In an embodiment, the composition is present in an amount effective for treatment and management of Polycystic Ovarian syndrome.

In an embodiment, the method includes administering to a patient a composition comprising *Saraca indica* (10 to 14 wt. %), *Symplocos* (8 to 12 wt. %), *Boerhavia diffusa* (8 to 12 wt. %), *Tinospora cordifolia* (2 to 5 wt. %), *Terminalia arjuna* (2 to 5 wt. %), *Saccharum officinarum* (2 to 5 wt. %), *Commiphora mukul* (5 to 8 wt. %) *Emblica officinalis* (≤2 wt. %), *Terminalia chebula* (≤2 wt. %), *Terminalia bellerica* (≤2 wt. %), *Stereospermum suaveolens* (≤2 wt. %), *Premna mucronata* (≤2 wt. %), *Gmelina arborea* (≤2 wt. %), *Aegle marmelos* (≤2 wt. %), *Oroxylum indicum* (≤2 wt. %), *Desmodium gangeticum* (≤2 wt. %), *Uraria picta* (≤2 wt. %), *Solanum indicum* (≤2 wt. %), *Solanum xanthocarpum* (≤2 wt. %), *Tribulus terrestris* (≤2 wt. %), *Sida cordifolia* (≤2 wt. %), *Nardostachys jatamansi* (≤3 wt. %), *Acacia catechu* (≤3 wt. %), *Rubia cordifolia* (≤3 wt. %), *Hemidesmus indicus* (≤2 wt. %), *Cedrus deodara* (≤3 wt. %), *Withania somnifera* (≤2 wt. %), *Pueraria tuberosa* (≤2 wt. %), *Hydnocarpus laurifolia* (≤2 wt. %), *Ficus glomerata* (≤2 wt. %), *Dioscorea bulbifera* (≤2 wt. %), *Cinnamomum camphora* (≤2 wt. %), *Acorus calamus* (≤2 wt. %), *Cyperus rotundus* (≤2 wt. %), *Swertia chirata* (≤2 wt. %), *Curcuma longa* (≤2 wt. %), *Aconitum heterophyllum* (≤2 wt. %), *Berberis aristata* (≤2 wt. %), *Plumbago zeylanica* (≤2 wt. %), *Coriandrum sativum* (≤2 wt. %), *Piper longum* (≤2 wt. %), *Embelia ribes* (≤2 wt. %), *Piper chaba* (≤2 wt. %), *Zingiber officinale* (≤2 wt. %), *Piper nigrum* (≤2 wt. %), *Operculina turpethum* (≤3 wt. %), *Baliospermum montanum* (≤3 wt. %), *Cinnamomum tamala* (≤3 wt. %), *Cinnamomum zeylanicum* (≤2 wt. %), *Bamboo manna* (≤3 wt. %), shilajit (5 to 8 wt. %), Makshika Bhasma (≤2 wt. %), Loha Bhasma (≤2 wt. %), and Kasisa Bhasma (≤2 wt. %), Yavakshara (≤2 wt %), Sarjikshara (≤2 wt %), Rock salt (≤2 wt %), Sonchal salt (≤2 wt %) and Black salt (≤2 wt %).

The embodiments of the disclosed method of treatment may be used as a primary line of treatment or as an adjunct to other treatment methods for PCOS.

The patient may be administered a therapeutically effective amount of the disclosed composition. The therapeutically effective amount may vary depending on the patient. In an embodiment, the therapeutically effective amount is 500 to 1000 mg administered one to three times a day. The disclosed composition (also referred as Test item or Test drug) was subjected to toxicity and efficacy studies, results of which are provided herein.

Toxicity Study

Test drug was administered once orally to overnight fasted female Wistar rats at 2000 and 5000 mg/kg body weight (2 steps/dose; 3 animals/step) at a dose volume 10 ml/kg. Body weight was recorded on day 0, 7 and 14. Mortality/Clinical signs were observed at approximately 30 minutes, 1, 2 and 4 h on day 0 (after test item administration) and thereafter once daily for 14 days.

All the experimental animals showed gain in body weight on day 7 and 14 in comparison to their day 0 body weight. No clinical signs and mortality were observed for 14 days in all experimental animals. No gross lesions were detected in animal treated with 2000 mg/kg body weight, whereas in animal number 8, treated with 5000 mg/kg body weight shows multifocal point of congestion in lungs. No gross lesions were detected in all other organs of experimental animals treated with 5000 mg/kg body weight.

Histopathologic examination of lungs of animal number 8 revealed alveolar haemorrhages, alveolar thickening with mononuclear cells infiltration and multifocal aggregates of mixed population of inflammatory cells around blood vessels and bronchioles.

Based on the observations, the $LD_{50}$ value of Test drug was found to be greater than 5000 mg/kg body weight and classified as Category-5 or unclassified based on Globally Harmonised Classification System (GHS) for Chemical Substances and Mixtures.

Efficacy study: To study the effect of Test drug in Letrozole induced polycystic ova syndrome in rats.

Procedure: Female (Nulliparous/Non-pregnant) Rat/Wistar Albino weighing about 150-180 g (obtained from Aditya Biolabs, Bangalore) were used for the study. Temperature and relative humidity were in the range of 19–25° C. and 30-70%, respectively and recorded. Animals were maintained in 12 h light artificial photoperiod and 12 h dark. Rats were housed in groups with 5 in each polypropylene cages (43L×27B×18H cm). Cages were covered with stainless steel grid top. Dried and dedusted corn cob was used as bedding material. Rats were provided with laboratory rodent feed. Reverse osmosis water was provided ad libitum. Acclimatization was for 7 days under laboratory conditions. Rats were marked with 0.1% picric acid on body for identification. Randomization was performed on last day of acclimatization. Rats with normal oestrous cycle were selected for the study. The Test drug was suspended in 0.5% carboxy methyl cellulose (CMC).

Induction of PCOS: All the experimental animals except control group, were orally administered with Letrozole at a dose of 1 mg/kg dissolved in 0.5% Carboxy Methyl Cellulose (CMC) once daily for 21 days (Demirel et al., 2016). Control group received vehicle only (0.5% CMC). Vaginal smears were taken third week of the study. Following the induction, female rats with PCOS were selected and grouped as shown in Table 7.

TABLE 7

Grouping of animals

| S. No. | Group | Treatment | No. of animals/group | Animal number |
|---|---|---|---|---|
| I | Vehicle control | 0.5% CMC (10 ml/kg, p.o) | 10 | 101-108 |
| II | Positive control | PCOS + 0.5% CMC (10 ml/kg, p.o) | 10 | 201-208 |
| III | Test item | PCOS + Test drug tablet (25 mg/kg) | 10 | 301-308 |
| IV | | PCOS + Test drug tablet (100 mg/kg) | 10 | 401-408 |
| V | | PCOS + Test drug tablet (400 mg/kg) | 10 | 501-508 |

Treatment: Test drug was administered orally at dosage volume of 10 ml/kg. Experimental animals were treated with vehicle/Test drug for a period of 21 days. At the end of the treatment period, blood samples were collected from retro orbito plexus of the experimental animals under ether anesthesia. Plasma was separated and further processed for biochemical and hormonal estimations. Following blood collection, all the survived animals' uterus and ovaries were harvested for histopathological examination.

Observations of the following parameters were made: Morbidity and mortality; Weekly body weight; Glucose, cholesterol, triglycerides, SGOT, SGPT, ALP and γ-GT (Spinreact, Spain); Serum hormones—FSH, LH, estrogen, progesterone and prolactin; and Uterus and ovaries histopathology (H&E staining)

Analysis: Data are expressed as mean±SEM. Mean difference between the groups were be analyzed by one way ANOVA followed multiple comparison test. P value≤0.05 was considered as statistically significant.

Table 8 depicts the effect of Test drug on sex hormones in PCOS rats. Table 9 depicts the effect of Test drug on plasma biochemical parameters in PCOS rats.

TABLE 8

Effect of Test drug on sex hormones in PCOS rats

| Groups | FSH (ng/mL) | LH (ng/mL) | Estrogen (ng/mL) | Progesterone (ng/mL) |
|---|---|---|---|---|
| Negative control | 3.62 ± 0.29 | 8.34 ± 0.83 | 877.46 ± 51.99 | 53.81 ± 5.05 |
| Positive control | 5.96 ± 0.61## | 26.24 ± 3.31## | 397.61 ± 57.59## | 25.22 ± 3.62## |
| Test drug (L) | 5.45 ± 0.58 | 22.58 ± 2.51 | 725.43 ± 90.26 | 28.56 ± 2.20 |
| Test drug (M) | 3.68 ± 0.20** | 11.62 ± 0.62** | 831.70 ± 61.05** | 49.92 ± 1.47** |
| Test drug (H) | 3.42 ± 0.24** | 12.74 ± 1.55** | 867.03 ± 72.76** | 54.87 ± 4.20** |

TABLE 9

Effect of Test drug on plasma biochemical parameters in PCOS rats

| Groups | Glucose (mg/dL) | Cholesterol (mg/dL) | TG (mg/dL) | SGOT (U/L) | SGPT (U/L) | Total Protein |
|---|---|---|---|---|---|---|
| Negative control | 89.23 ± 3.66 | 43.10 ± 3.91 | 48.15 ± 5.05 | 65.02 ± 4.52 | 39.38 ± 1.49 | 5.05 ± 0.11 |
| Positive control | 136.40 ± 6.69## | 70.86 ± 7.51## | 83.76 ± 4.03## | 72.09 ± 4.52 | 54.32 ± 3.53 | 5.61 ± 0.14 |
| Test drug (L) | 127.15 ± 6.70 | 51.40 ± 5.69* | 71.92 ± 6.55 | 71.39 ± 4.04 | 35.32 ± 3.82 | 5.44 ± 0.19 |
| Test drug (M) | 87.96 ± 2.79** | 35.79 ± 1.78** | 54.63 ± 5.52** | 76.76 ± 3.33 | 41.35 ± 5.86 | 5.82 ± 0.22 |
| Test drug (H) | 88.39 ± 3.4** | 40.57 ± 1.21** | 56.11 ± 6.06** | 50.87 ± 2.98 | 25.18 ± 1.14 | 5.47 ± 0.22 |

Results: No significant difference in body weight changes between the groups; Test drug restored the altered (letrazole induced) estrus cycle in female the rats; Test drug decreased glucose, cholesterol, and triglycerides levels in PCOS animals; Test drug restored the biochemical and improved the hormonal levels in the PCOS rats. Test drug improved biochemicals (particularly glucose and cholesterol) and sex hormonal status is PCOS rats.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. An oral composition for treatment and management of Polycystic Ovarian syndrome, comprising therapeutically effective amount of *Saraca indica, Symplocos racemosa, Boerhavia diffusa, Tinospora cordifolia, Terminalia arjuna, Saccharum officinarum* and *Commiphora mukul*, or extracts thereof; Shilajit; at least one bhasma; and a suitable excipient.

2. The composition as claimed in claim 1, wherein said bhasma is selected from the group consisting of Swarna Makshika Bhasma, Loha Bhasma, and Kasisa Bhasma.

3. The composition as claimed in claim 1, further comprising at least one ingredient selected from the group consisting of *Emblica officinalis, Terminalia chebula, Terminalia bellerica, Stereospermum suaveolens, Premna mucronata, Gmelina arborea, Aegle marmelos, Oroxylum indicum, Desmodium gangeticum, Uraria picta, Solanum indicum, Solanum xanthocarpum, Tribulus terrestris, Sida cordifolia, Nardostachys jatamansi, Acacia catechu, Rubia cordifolia, Hemidesmus indicus, Cedrus deodara, Withania somnifera, Pueraria tuberosa, Hydnocarpus laurifolia, Ficus glomerata, Dioscorea bulbifera, Cinnamomum camphora, Acorus calamus, Cyperus rotundus, Swertia chirata, Curcuma longa, Aconitum heterophyllum, Berberis aristata, Plumbago zeylanica, Coriandrum sativum, Piper longum, Embelia ribes, Piper chaba, Zingiber officinale, Piper nigrum, Operculina turpethum, Baliospermum montanum, Cinnamomum tamala, Cinnamomum zeylanicum* and *Bamboo manna*, or extracts thereof.

4. The composition as claimed in claim 1, wherein said *Saraca indica* is present in an amount in the range of 10 to 14 wt. %; *Symplocos racemosa* is present in an amount in the range of 8 to 12 wt. %; *Boerhavia diffusa* is present in an amount in the range of 8 to 12 wt. %; *Tinospora cordifolia* is present in an amount in the range of 2 to 5 wt. %; *Terminalia arjuna* is present in an amount in the range of 2 to 5 wt. %; *Saccharum officinarum* is present in an amount in the range of 2 to 5 wt. %; and *Commiphora mukul* is present in an amount in the range of 5 to 8 wt. %, of the total composition.

5. The composition as claimed in claim 1, wherein said shilajit is present in an amount in the range of 5 to 8 wt. %, of the total composition.

6. The composition as claimed in claim 1, wherein said bhasma is present in an amount of ≤2 wt. %, of the total composition.

7. The composition as claimed in claim 2, wherein said Swarna Makshika Bhasma is present in an amount of ≤2 wt. %; Loha Bhasma is present in an amount of ≤2 wt. %; and Kasisa Bhasma is present in an amount of ≤2 wt. %, of the total composition.

8. The composition as claimed in claim 1, said composition further comprising at least one alkali selected from a group consisting of Yavakshara and Sarjikshara.

9. The composition as claimed in claim 8, wherein said Yavakshara is present in an amount of ≤2 wt %, and Sarjikshara is present in an amount of ≤2 wt %.

10. The composition as claimed in claim 1, said composition further comprising at least one salt selected from a group consisting of Black salt, Sonchal salt and Rock salt.

11. The composition as claimed in claim 10, wherein said Rock salt is present in an amount of ≤2 wt %, Black salt is present in an amount of ≤2 wt %, and Sonchal salt is present in an amount of ≤2 wt %.

12. The composition as claimed in claim 3, wherein said *Emblica officinalis* is present in an amount of ≤2 wt. %; *Terminalia chebula* is present in an amount of ≤2 wt. %; *Terminalia bellerica* is present in an amount of ≤2 wt. %; *Stereospermum suaveolens* is present in an amount of ≤2 wt. %; *Premna mucronata* is present in an amount of ≤2 wt. %; *Gmelina arborea* is present in an amount of ≤2 wt. %; *Aegle marmelos* is present in an amount of ≤2 wt. %; *Oroxylum indicum* is present in an amount of ≤2 wt. %; *Desmodium gangeticum* is present in an amount of ≤2 wt. %; *Uraria picta* is present in an amount of ≤2 wt. %; *Solanum indicum* is present in an amount of ≤2 wt. %; *Solanum xanthocarpum* is present in an amount of ≤2 wt. %; *Tribulus terrestris* is present in an amount of ≤2 wt. %; *Sida cordifolia* is present in an amount of ≤2 wt. %; *Nardostachys jatamansi* is present in an amount of ≤3 wt. %; *Acacia catechu* is present in an amount of ≤3 wt. %; *Rubia cordifolia* is present in an amount of ≤3 wt. %; *Hemidesmus indicus* is present in an amount of ≤2 wt. %; *Cedrus deodara* is present in an amount of ≤3 wt. %; *Withania somnifera* is present in an amount of ≤2 wt. %; *Pueraria tuberosa* is present in an amount of ≤2 wt. %; *Hydnocarpus laurifolia* is present in an amount of ≤2 wt. %; *Ficus glomerata* is present in an amount of ≤2 wt. %, *Dioscorea bulbifera* is present in an amount of ≤2 wt. %; *Cinnamomum camphora* is present in an amount of ≤2 wt. %; *Acorus calamus* is present in an amount of ≤2 wt. %; *Cyperus rotundus* is present in an amount of ≤2 wt. %; *Swertia chirata* is present in an amount of ≤2 wt. %; *Curcuma longa* is present in an amount of ≤2 wt. %; *Aconitum heterophyllum* is present in an amount of ≤2 wt. %; *Berberis aristata* is present in an amount of ≤2 wt. %; *Plumbago zeylanica* is present in an amount of ≤2 wt. %; *Coriandrum sativum* is present in an amount of ≤2 wt. %; *Piper longum* is present in an amount of ≤2 wt. %; *Embelia ribes* is present in an amount of ≤2 wt. %; *Piper chaba* is present in an amount of ≤2 wt. %; *Zingiber officinale* is present in an amount of ≤2 wt. %; *Piper nigrum* is present in an amount of ≤2 wt. %; *Operculina turpethum* is present in an amount of ≤3 wt. %; *Baliospermum montanum* is present in an amount of ≤3 wt. %; *Cinnamomum tamala* is present in an amount of ≤3 wt. %; *Cinnamomum zeylanicum* is present in an amount of ≤2 wt. %; and *Bamboo manna* is present in an amount of ≤3 wt. %, of the total weight of the composition.

13. The composition as claimed in claim 1, further comprising Gum *acacia*.

14. The composition as claimed in claim 13, wherein Gum acacia is present in an amount in the range of 8 to 12 wt. % of the total composition.

15. The composition as claimed in claim 1, said composition comprising *Saraca indica, Symplocos racemosa, Boerhavia diffusa, Tinospora cordifolia, Terminalia arjuna, Saccharum officinarum, Commiphora mukul, Emblica officinalis, Terminalia chebula, Terminalia bellerica, Stereospermum suaveolens, Premna mucronata, Gmelina arborea, Aegle marmelos, Oroxylum indicum, Desmodium gangeticum, Uraria pitta, Solanum indicum, Solanum xanthocarpum, Tribulus terrestris, Sida cordifolia, Nardostachys jatamansi, Acacia catechu, Rubia cordifolia, Hemidesmus indicus, Cedrus deodara, Withania somnifera, Pueraria tuberosa, Hydnocarpus laurifolia, Ficus glomerata, Dioscorea bulbifera, Cinnamomum camphora, Acorus calamus, Cyperus rotundus, Swertia chirata, Curcuma longa, Aconitum heterophyllum, Berberis aristata, Plumbago zeylanica, Coriandrum sativum, Piper longum, Embelia ribes, Piper chaba, Zingiber officinale, Piper nigrum, Operculina turpethum, Baliospermum montanum, Cinnamomum tamala, Cinnamomum zeylanicum, Bamboo manna,* Shilajit, Swarna Makshika Bhasma, Loha Bhasma, Kasisa Bhasma, Yavakshara, Sarjikshara, Black salt, Sonchal salt and Rock salt.

16. The composition as claimed in claim 1, wherein said composition is in at least one form selected from the group consisting of tablets, pellets, lozenges, granules, suspensions and capsules.

17. A method for treatment and management of Polycystic ovarian syndrome, said method comprising administering, to a patient in need thereof, a therapeutically effective amount of the composition claimed in claim 1.

18. A method for treatment and management of symptoms of polycystic ovarian syndrome, said method comprising administering, to a patient in need thereof, a therapeutically effective amount of the composition claimed in claim 1.

19. A method for improving reproductive health of an individual, said method comprising administering, to said individual, the composition claimed in claim 1.

* * * * *